(12) United States Patent
Kim et al.

(10) Patent No.: US 10,538,599 B2
(45) Date of Patent: Jan. 21, 2020

(54) MODIFIED POLYMER, METHOD OF PREPARING THE SAME, AND RUBBER COMPOSITION INCLUDING THE MODIFIED POLYMER

(71) Applicant: LG Chem, Ltd., Seoul (KR)

(72) Inventors: Min Soo Kim, Daejeon (KR); Seung Ho Choi, Daejeon (KR); Dae June Joe, Daejeon (KR); Won Mun Choi, Daejeon (KR)

(73) Assignee: LG Chem, Ltd. (KR)

( * ) Notice: Subject to any disclaimer, the term of this patent is extended or adjusted under 35 U.S.C. 154(b) by 74 days.

(21) Appl. No.: 15/554,544

(22) PCT Filed: Dec. 1, 2016

(86) PCT No.: PCT/KR2016/014062
§ 371 (c)(1),
(2) Date: Aug. 30, 2017

(87) PCT Pub. No.: WO2017/105012
PCT Pub. Date: Jun. 22, 2017

(65) Prior Publication Data
US 2018/0072851 A1    Mar. 15, 2018

(30) Foreign Application Priority Data
Dec. 18, 2015 (KR) .................. 10-2015-0181692

(51) Int. Cl.
| | | |
|---|---|---|
| *C08C 19/22* | (2006.01) | |
| *C08C 19/25* | (2006.01) | |
| *C08C 19/44* | (2006.01) | |
| *C08F 236/10* | (2006.01) | |
| *C08F 236/06* | (2006.01) | |
| *C07C 39/20* | (2006.01) | |
| *C07C 43/215* | (2006.01) | |
| *C07F 1/02* | (2006.01) | |
| *C08F 212/08* | (2006.01) | |
| *C08G 81/02* | (2006.01) | |
| *C08K 5/544* | (2006.01) | |
| *C08K 5/56* | (2006.01) | |
| *C08K 3/011* | (2018.01) | |
| *C08K 3/06* | (2006.01) | |
| *C08L 9/06* | (2006.01) | |

(52) U.S. Cl.
CPC .............. *C08C 19/22* (2013.01); *C07C 39/20* (2013.01); *C07C 43/215* (2013.01); *C07F 1/02* (2013.01); *C08C 19/25* (2013.01); *C08C 19/44* (2013.01); *C08F 212/08* (2013.01); *C08F 236/06* (2013.01); *C08F 236/10* (2013.01); *C08G 81/025* (2013.01); *C08K 5/544* (2013.01); *C08K 5/56* (2013.01); *C08K 3/011* (2018.01); *C08K 3/06* (2013.01); *C08L 9/06* (2013.01)

(58) Field of Classification Search
CPC .......... C08F 8/30; C08F 212/08; C08F 12/08; C08C 19/22; C08C 19/25; C08C 19/44; C08L 25/06; C08L 25/08; C08L 25/10; C08K 5/544
See application file for complete search history.

(56) References Cited

U.S. PATENT DOCUMENTS

| | | |
|---|---|---|
| 2008/0300340 A1 | 12/2008 | Gross et al. |
| 2009/0270558 A1 | 10/2009 | Gandon-pain et al. |
| 2009/0292043 A1 | 11/2009 | Kurazumi et al. |
| 2011/0077325 A1 | 3/2011 | Luo |
| 2014/0187723 A1 | 7/2014 | Hsieh et al. |
| 2014/0206793 A1* | 7/2014 | Okabe ...................... C08K 3/36 523/156 |
| 2016/0208024 A1 | 7/2016 | Kim et al. |

FOREIGN PATENT DOCUMENTS

| | | |
|---|---|---|
| CN | 101133105 A | 2/2008 |
| CN | 101160328 A | 4/2008 |
| CN | 103764746 A | 4/2014 |
| JP | H07228686 A | 8/1995 |
| JP | H11158413 A | 6/1999 |

(Continued)

OTHER PUBLICATIONS

Search report from International Application No. PCT/KR2016/014062, dated Mar. 8, 2017.
Extended European Search Report for Application No. EP16875954.6 dated Mar. 14, 2018.
Fengjun Hua et al., Temperature-induced phase-transitions of methoxyoligo(oxyethylene) styrene-based block copolymers in aqueous solution, Soft Matter, vol. 9, No. 37, 2013, p. 8897, XP055445482.
Sinta et al., "Cation and Anion Binding Properties of Poly(vinylbenzoglymes)", Macromolecules, 1980, vol. 13, pp. 339-345, XP055445504, Retrieved from Internet: URL:http://pubs.acs.org/doi/pdf/10.1021/ma60074a025 [retrieved on Jan. 29, 2018].
Chinese Search Report for Application 201680024033.7 dated Jul. 23, 2019.

*Primary Examiner* — Roberto Rabago
(74) *Attorney, Agent, or Firm* — Lerner, David, Littenberg, Krumholz & Mentlik, LLP

(57) ABSTRACT

The present invention relates to a modified polymer having a high modification ratio and an excellent affinity with a filler, a method of preparing the same, a rubber composition including the modified polymer, and a molded article prepared from the rubber composition. The modified polymer according to the present invention may exhibit a high modification ratio by including functional groups in a polymer main chain and on at least one end thereof, and thus, an affinity with a filler, such as silica, may be excellent. Also, the rubber composition according to the present invention may have excellent processability by including the modified polymer having an excellent affinity with the filler, and, as a result, a processed product (e.g., tire) prepared by using the rubber composition may have excellent tensile strength, abrasion resistance, and wet road surface resistance.

20 Claims, No Drawings

(56) References Cited

FOREIGN PATENT DOCUMENTS

| | | | |
|---|---|---|---|
| JP | 2004018587 | A | 1/2004 |
| JP | 2010528111 | A | 8/2010 |
| JP | 2013060525 | A | 4/2013 |
| JP | 2013119557 | A | 6/2013 |
| JP | 2013216828 | A | 10/2013 |
| JP | 2014129514 | A | 7/2014 |
| JP | 2015067720 | A | 4/2015 |
| JP | 2015196684 | A | 11/2015 |
| JP | 2015 218288 | * | 12/2015 |
| JP | 2015218288 | A | 12/2015 |
| KR | 20120088733 | A | 8/2012 |
| KR | 20150131465 | A | 11/2015 |
| WO | 2015056994 | A1 | 4/2015 |
| WO | 2016104931 | A1 | 6/2016 |

* cited by examiner

MODIFIED POLYMER, METHOD OF PREPARING THE SAME, AND RUBBER COMPOSITION INCLUDING THE MODIFIED POLYMER

CROSS-REFERENCE TO RELATED APPLICATIONS

The present application is a national phase entry under 35 U.S.C. § 371 of International Application No. PCT/KR2016/014062, filed Dec. 1, 2016, published in Korean, which claims priority from Korean Patent Application No. 10-2015-0181692, filed on Dec. 18, 2015, in the Korean Intellectual Property Office, the disclosures of which are incorporated herein by reference.

TECHNICAL FIELD

The present invention relates to a modified polymer having a high modification ratio and an excellent affinity with a filler, a method of preparing the same, a rubber composition including the modified polymer, and a molded article prepared from the rubber composition.

BACKGROUND ART

In line with the recent demand for fuel-efficient cars, a polymer having adjustment stability represented by wet skid resistance as well as low rolling resistance and excellent abrasion resistance and tensile properties is required as a rubber material for a tire.

In order to reduce the rolling resistance of a tire, there is a method of reducing a hysteresis loss of a vulcanized rubber, and rebound resilience at 50° C. to 80° C., tan 5, or Goodrich heat generation is used as an evaluation index of the vulcanized rubber. That is, it is desirable to use a rubber material having high rebound resilience at the above temperature or low tan 5 or Goodrich heat generation at the above temperature.

A natural rubber, a polyisoprene rubber, or a polybutadiene rubber is known as a rubber material having a low hysteresis loss, but these rubbers may have low wet skid resistance. Thus, recently, a conjugated diene-based (co) polymer, such as a styrene-butadiene rubber (hereinafter, referred to as "SBR") or a butadiene rubber (hereinafter, referred to as "BR"), is prepared by emulsion polymerization or solution polymerization to be used as a rubber for a tire. Among these polymerizations, the greatest advantage of the solution polymerization in comparison to the emulsion polymerization is that a vinyl structure content and a styrene content, which specify physical properties of the rubber, may be arbitrarily adjusted and its molecular weight and physical properties may be controlled by coupling or modification. Thus, the SBR prepared by the solution polymerization is widely used as a rubber material for a tire because it is easy to change a structure of the finally prepared SBR or BR, and movement of chain ends may be reduced and a coupling force with a filler, such as silica or carbon black, may be increased by coupling or modification of the chain ends.

In a case in which the solution-polymerized SBR is used as the rubber material for a tire, since a glass transition temperature of the rubber is increased by increasing a vinyl content in the SBR, physical properties, such as running resistance and braking force, required for a tire may not only be controlled, but fuel consumption may also be reduced by appropriately adjusting the glass transition temperature.

The solution-polymerized SBR is prepared by using an anionic polymerization initiator, and is being used by coupling or modification of chain ends of the formed polymer using various modifiers.

Carbon black and silica are being used as a reinforcing filler of a tire's tread, wherein, in a case in which the silica is used as the reinforcing filler, the hysteresis loss may be low and the wet skid resistance may be improved. However, since the silica having a hydrophilic surface has a low affinity with the rubber in comparison to the carbon black having a hydrophobic surface, dispersibility may be poor, and, thus, there is a need to use a separate silane coupling agent to improve the dispersibility or provide coupling between the silica and the rubber.

Therefore, a method of introducing a functional group having an affinity or reactivity with the silica into the ends of rubber molecules is being performed, but its effect is insufficient.

DISCLOSURE OF THE INVENTION

Technical Problem

The present invention provides a modified polymer including a substituted styrene-based compound-derived functional group represented by Formula 1 and a modifier-derived function group represented by Formula 2.

The present invention also provides a method of preparing the modified polymer.

The present invention also provides a rubber composition including the modified polymer.

The present invention also provides a molded article prepared from the rubber composition.

Technical Solution

According to an aspect of the present invention, there is provided a modified polymer including a substituted styrene-based compound-derived functional group represented by Formula 1 and a modifier-derived function group represented by Formula 2.

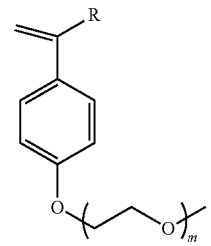

[Formula 1]

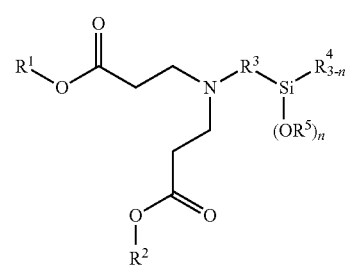

[Formula 2]

In Formula 1 or 2,

R is a hydrogen atom or a monovalent hydrocarbon group having 1 to 20 carbon atoms, $R^1$ and $R^2$ are each independently a monovalent hydrocarbon group having 1 to 20 carbon atoms, or a monovalent hydrocarbon group having 1 to 20 carbon atoms which includes at least one heteroatom selected from the group consisting of nitrogen (N), sulfur (S), and oxygen (O), $R^3$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, $R^4$ and $R^5$ are each independently a monovalent hydrocarbon group having 1 to 20 carbon atoms, m is an integer of 1 to 11, and n is an integer of 1 to 3.

According to another aspect of the present invention, there is provided a method of preparing the modified polymer according to an embodiment of the present invention includes the steps of: performing a polymerization reaction of a monomer with a substituted styrene-based compound represented by Formula 1 in a hydrocarbon solvent in the presence of an organometallic compound to prepare an active polymer coupled with an organometal (step 1); and reacting the active polymer with a modifier represented by Formula 2 (step 2).

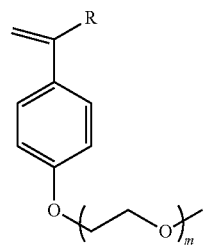

[Formula 1]

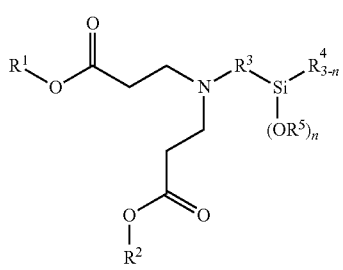

[Formula 2]

In Formula 1 or 2,

R is a hydrogen atom or a monovalent hydrocarbon group having 1 to 20 carbon atoms, $R^1$ and $R^2$ are each independently a monovalent hydrocarbon group having 1 to 20 carbon atoms, or a monovalent hydrocarbon group having 1 to 20 carbon atoms which includes at least one heteroatom selected from the group consisting of nitrogen (N), sulfur (S), and oxygen (O), $R^3$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, $R^4$ and $R^5$ are each independently a monovalent hydrocarbon group having 1 to 20 carbon atoms, m is an integer of 1 to 11, and n is an integer of 1 to 3.

According to another aspect of the present invention, there is provided a rubber composition including the modified polymer.

According to another aspect of the present invention, there is provided a molded article prepared from the rubber composition.

Advantageous Effects

A modified polymer according to the present invention may exhibit a high modification ratio by including a substituted styrene-based compound-derived functional group represented by Formula 1 and a modifier-derived function group represented by Formula 2, and thus, an affinity with a filler, such as silica, may be excellent.

Also, in a method of preparing a modified polymer according to the present invention, since a substituted styrene-based compound represented by Formula 1 may act as a polar solvent by using the compound during polymerization, a coupling reaction with an active site of the polymer may be easily performed. Thus, since the use of the polar solvent may be reduced, an economic advantage may not only be obtained, but also a functional group may be easily introduced into a polymer main chain. Furthermore, since modification is performed by using a modifier represented by Formula 2, a modified polymer having a high modification ratio may be easily prepared due to high solubility of the modifier.

In addition, a rubber composition according to the present invention may have excellent processability by including the modified polymer having an excellent affinity with the filler, and, as a result, a processed product (e.g., tire) prepared by using the rubber composition may have excellent tensile strength, abrasion resistance, and wet road surface resistance.

Therefore, the modified polymer according to the present invention, the preparation method thereof, the rubber composition including the modified polymer, and a molded article prepared from the composition may be suitable for industries that need the modified polymer, for example, tire industry.

MODE FOR CARRYING OUT THE INVENTION

Hereinafter, the present invention will be described in more detail to allow for a clearer understanding of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention provides a modified polymer which may exhibit excellent processability due to a high affinity with a filler.

The modified polymer according to an embodiment of the present invention includes a substituted styrene-based compound-derived functional group represented by Formula 1 and a modifier-derived function group represented by Formula 2.

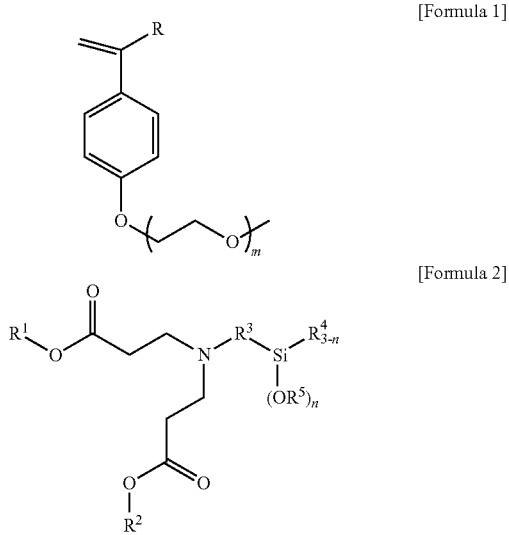

[Formula 1]

[Formula 2]

In Formula 1 or 2,

R is a hydrogen atom or a monovalent hydrocarbon group having 1 to 20 carbon atoms, $R^1$ and $R^2$ are each independently a monovalent hydrocarbon group having 1 to 20 carbon atoms, or a monovalent hydrocarbon group having 1 to 20 carbon atoms which includes at least one heteroatom selected from the group consisting of nitrogen (N), sulfur (S), and oxygen (O), $R^3$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, $R^4$ and $R^5$ are each independently a monovalent hydrocarbon group having 1 to 20 carbon atoms, m is an integer of 1 to 11, and n is an integer of 1 to 3.

The modified polymer according to the embodiment of the present invention may be prepared by a preparation method to be described later, the substituted styrene-based compound-derived functional group represented by Formula 1 may be bonded to a main chain, and the modifier-derived function group represented by Formula 2 may be bonded to at least one end thereof. That is, the modified polymer according to the present invention may include a functional group on the at least one end as well as the main chain, and thus, physical properties may be improved.

The expression "at least" used in the present invention denotes a minimum value, and, for example, the expression "at least one end" may denote minimum one end, that is, one end or one or more ends.

Specifically, the substituted styrene-based compound represented by Formula 1 may be a modified monomer for polymer modification, and may provide a function group which may change physical properties of the modified polymer modified by using the compound.

For example, the substituted styrene-based compound represented by Formula 1 may be bonded to the polymer main chain by being used as a modified monomer, and thus, the functional group may be introduced into the polymer in high yield. Also, the substituted styrene-based compound may include an inorganic filler affinity functional group which may improve abrasion resistance and processability of a rubber composition by interaction with an inorganic filler. The inorganic filler affinity functional group is specifically an ethylene glycol group, wherein it may improve the abrasion resistance and processability of the polymer by a condensation reaction with a functional group of the surface of the inorganic filler, for example, a silanol group of the surface of silica when the inorganic filler is the silica, after being introduced into the polymer. Furthermore, since the substituted styrene-based compound includes the ethylene glycol group, the substituted styrene-based compound may act as a polar solvent used in polymer polymerization, and thus, the use of the polar solvent may be reduced.

In Formula 1, R may be a hydrogen atom, an alkyl group having 1 to 20 carbon atoms, a cycloalkyl group having 3 to 20 carbon atoms, an aryl group having 6 to 20 carbon atoms, an arylalkyl group having 7 to 20 carbon atoms, an alkoxy group having 1 to 20 carbon atoms, an alkoxyalkyl group having 2 to 20 carbon atoms, or a phenoxyalkyl group having 7 to 20 carbon atoms.

Specifically, in Formula 1, R may be a hydrogen atom, and m may be an integer of 1 to 11.

Also, the modifier represented by Formula 2, as a functional group capable of improving the physical properties of the modified polymer, may include at least one of a functional group for improving dispersibility of inorganic filler, an inorganic filler affinity functional group, and a solvent affinity functional group.

Specifically, the modifier of Formula 2 may modify the polymer at a high modification ratio by including an ester group having high reactivity with respect to an active site of an active polymer, and, as a result, the functional group substituted with the modifier may be introduced into the polymer in high yield. Furthermore, the modifier is a functional group capable of improving the dispersibility of the inorganic filler by preventing agglomeration of the inorganic filler in the rubber composition, wherein the modifier may include an amino group, particularly, a tertiary amino group. For example, in a case in which silica is used as the inorganic filler, agglomeration may easily occur due to a hydrogen bond between hydroxide groups present on the surface thereof. Thus, dispersibility of the silica may be improved by allowing the tertiary amino group in the modifier to disturb the hydrogen bond between the hydroxide groups. Also, the modifier may include at least one of the inorganic filler affinity functional group capable of improving the abrasion resistance and processability of the rubber composition by the interaction with the inorganic filler along with the above-described amino group and the solvent affinity functional group having an excellent affinity with a solvent used in a modification reaction of the polymer. The inorganic filler affinity functional group is specifically an alkoxysilyl group, wherein it may improve the abrasion resistance and processability of the polymer by a condensation reaction with a functional group of the surface of the inorganic filler, for example, a silanol group of the surface of silica when the inorganic filler is the silica, after being introduced into the polymer. Such an improvement effect may be enhanced as the number of the alkoxysilyl groups is increased. Furthermore, the solvent affinity functional group is specifically a hydrocarbon group, such as an alkyl group or an aryl group, wherein the solvent affinity functional group may increase solubility of the modifier in the solvent during the modification process of the polymer, and, as a result, a modification ratio of the polymer may be improved.

In a case in which the number of the alkoxysilyl groups is increased to increase the modification ratio and improve the affinity with the filler, Mooney viscosity may be increased and viscosity during storage may be increased due to hydrolysis and condensation reaction, but, since the modifier according to an embodiment of the present invention includes two carbonyl groups having high reactivity with anions, the modifier may not only suppress the increase in the Mooney viscosity due to the hydrolysis and condensation reaction, but may also allow the polymer to selectively react with the carbonyl group by further increasing anion reactivity.

In Formula 2, $R^1$ and $R^2$ are each independently a monovalent hydrocarbon group having 1 to 20 carbon atoms, or a monovalent hydrocarbon group having 1 to 20 carbon atoms which includes at least one heteroatom selected from the group consisting of N, S, and O.

Also, in a case in which $R^1$ and $R^2$ are each independently a monovalent hydrocarbon group having 1 to 20 carbon atoms, $R^1$ and $R^2$ may each independently be selected from the group consisting of an alkyl group having 1 to 20 carbon atoms, a cycloalkyl group having 3 to 20 carbon atoms, an aryl group having 6 to 20 carbon atoms, and an arylalkyl group having 7 to 20 carbon atoms. Specifically, $R^1$ and $R^2$ may each independently be an alkyl group having 1 to 10 carbon atoms, a cycloalkyl group having 3 to 12 carbon atoms, an aryl group having 6 to 12 carbon atoms, or an arylalkyl group having 7 to 12 carbon atoms.

Furthermore, in a case in which $R^1$ and $R^2$ are each independently a monovalent hydrocarbon group having 1 to 20 carbon atoms which includes a heteroatom, $R^1$ and $R^2$ may each independently be one including a heteroatom instead of at least one carbon atom in the hydrocarbon group; or may each independently be one in which at least one hydrogen atom bonded to the carbon atom in the hydrocarbon group is substituted with a heteroatom or a functional group including a heteroatom, and, in this case, the heteroatom may be selected from the group consisting of N, S, and O.

Specifically, in a case in which $R^1$ and $R^2$ are each independently a monovalent hydrocarbon group having 1 to 20 carbon atoms which includes a heteroatom, $R^1$ and $R^2$ may each independently be an alkoxy group; a phenoxy group; a carboxy group; an acid anhydride group; an amino group; an amide group; an epoxy group; a mercapto group; and a hydrocarbon group (e.g., hydroxyalkyl group, alkoxyalkyl group, phenoxyalkyl group, aminoalkyl group, or thiolalkyl group) having 1 to 20 carbon atoms which includes at least one functional group selected from the group consisting of a hydroxy group, an alkoxy group, a phenoxy group, a carboxy group, an ester group, an acid anhydride group, an amino group, an amide group, an epoxy group, and a mercapto group. For example, in a case in which $R^1$ and $R^2$ are each independently a monovalent hydrocarbon group having 1 to 20 carbon atoms which includes a heteroatom, $R^1$ and $R^2$ may each independently be selected from the group consisting of an alkoxy group having 1 to 20 carbon atoms, an alkoxyalkyl group having 2 to 20 carbon atoms, a phenoxyalkyl group having 7 to 20 carbon atoms, and an aminoalkyl group having 1 to 20 carbon atoms. Specifically, $R^1$ and $R^2$ may each independently be an alkoxyalkyl group having 2 to 10 carbon atoms.

Also, in Formula 2, $R^3$ may be an alkylene group having 1 to 6 carbon atoms, and, specifically, $R^3$ may be an alkylene group having 1 to 3 carbon atoms.

Furthermore, in Formula 2, $R^4$ and $R^5$ may each independently be an alkyl group having 1 to 10 carbon atoms, and, specifically, $R^4$ and $R^5$ may each independently be an alkyl group having 1 to 5 carbon atoms.

In addition, in Formula 2, n may be an integer of 1 to 3, and, specifically, n may be an integer of 2 or 3.

Also, the modifier may have a solubility in a nonpolar solvent, for example, hexane, of 3 wt % or more at 25° C. and 1 atmosphere. Herein, the solubility of the modifier denotes a degree to which the modifier is clearly dissolved without a turbidity phenomenon during visual observation. Since the modifier has high solubility as described above, a high modification ratio for the polymer may be achieved.

The modified polymer may be a homopolymer including an aromatic vinyl-based monomer-derived unit. Also, the modified polymer may be a copolymer including an aromatic vinyl-based monomer-derived unit and a conjugated diene-based monomer-derived unit.

The expression "derived unit" used in the present invention may denote a component or structure generated from a certain material or may denote the material itself.

Furthermore, in a case in which the modified polymer is a copolymer, the copolymer may be a random copolymer.

The expression "random copolymer" in the present invention may denote that constituent units constituting the copolymer are disorderly arranged.

The conjugated diene-based monomer is not particularly limited, but, for example, may be at least one selected from the group consisting of 1,3-butadiene, 2,3-dimethyl-1,3-butadiene, piperylene, 3-butyl-1,3-octadiene, isoprene, and 2-phenyl-1,3-butadiene.

In a case in which the modified polymer is a copolymer, the modified polymer may include the conjugated diene-based monomer-derived unit in an amount of 60 wt % or more, particularly 60 wt % to 90 wt %, and more particularly 60 wt % to 85 wt %.

The aromatic vinyl-based monomer is not particularly limited, but, for example, may be at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene.

In a case in which the modified polymer is a copolymer, the modified polymer may include the aromatic vinyl-based monomer-derived unit in an amount of 40 wt % or less, particularly 10 wt % to 40 wt %, and more particularly 15 wt % to 40 wt %.

Also, the modified polymer may have a molecular weight distribution (Mw/Mn) of 1.01 to 10, particularly 1.05 to 5, and more particularly 1.1 to 3. Furthermore, the modified polymer may have a weight-average molecular weight of 10,000 g/mol to 2,000,000 g/mol, and particularly 100,000 g/mol to 2,000,000 g/mol. In a case in which the modified polymer has the above-described molecular weight distribution, the processability of the rubber composition including the modified polymer may be improved, and, as a result, mechanical properties, low fuel consumption property, and abrasion resistance of a molded article prepared may be improved.

The modified polymer may have a vinyl content of 5 wt % or more, particularly 10 wt % or more, and more particularly 15 wt % to 70 wt %. In a case in which the vinyl content of the modified polymer is within the above range, since a glass transition temperature may be adjusted to an appropriate range, physical properties, such as running resistance and braking force, required for a tire may not only be satisfied when applied to the tire, but it also has an effect of reducing fuel consumption.

Herein, the vinyl content denotes a content of a 1,2-added conjugated diene-based monomer rather than a 1,4-added conjugated diene-based monomer based on 100 wt % of a polymer composed of a monomer having a vinyl group and an aromatic vinyl-based monomer.

Also, the present invention provides a method of preparing the modified polymer.

The method of preparing the modified polymer according to an embodiment of the present invention includes the steps of: performing a polymerization reaction of a monomer with a substituted styrene-based compound represented by Formula 1 in a hydrocarbon solvent in the presence of an organometallic compound to prepare an active polymer coupled with an organometal (step 1); and reacting the active polymer with a modifier represented by Formula 2 (step 2).

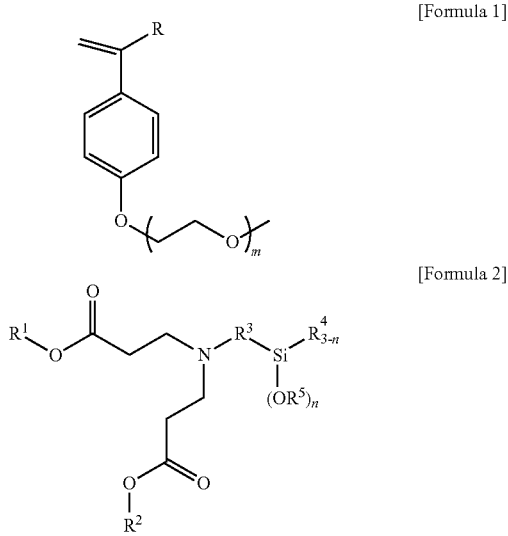

[Formula 1]

[Formula 2]

In Formula 1 or 2,

R is a hydrogen atom or a monovalent hydrocarbon group having 1 to 20 carbon atoms, $R^1$ and $R^2$ are each independently a monovalent hydrocarbon group having 1 to 20 carbon atoms, or a monovalent hydrocarbon group having 1 to 20 carbon atoms which includes at least one heteroatom selected from the group consisting of N, S, and O, $R^3$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms, $R^4$ and $R^5$ are each independently a monovalent hydrocarbon group having 1 to 20 carbon atoms, m is an integer of 1 to 11, and n is an integer of 1 to 3.

Step 1 is a step for preparing an active polymer coupled with a functional group derived from a substituted styrene-based compound represented by Formula 1 and an organometal, wherein step 1 may be performed by polymerization of a monomer with the styrene-based compound represented by Formula 1 in a hydrocarbon solvent in the presence of an organometallic compound. That is, in the preparation method according to the embodiment of the present invention, since the substituted styrene-based compound represented by Formula 1 is used as a modified monomer to perform polymerization with a monomer constituting a polymer main chain, the polymer main chain may be polymerized and, simultaneously, a function group may be introduced into the main chain. Thus, the polymerization of step 1 may be a first modification step.

Herein, the monomer may vary depending on the desired polymer, and, for example, in a case in which the desired polymer is a homopolymer including an aromatic vinyl-based monomer-derived unit, the monomer may be an aromatic vinyl-based monomer alone, and, in a case in which the desired polymer is a copolymer including an aromatic vinyl-based monomer-derived unit and a conjugate diene-based monomer-derived unit, the monomer may be a mixture of an aromatic vinyl-based monomer and a conjugate diene-based monomer.

Specific types of the aromatic vinyl-based monomer and the conjugate diene-based monomer may be the same as those described above, and an amount of each monomer used may be appropriately adjusted within a range in which the aromatic vinyl-based monomer-derived unit and the conjugate diene-based monomer-derived unit may be controlled within the above-described ranges.

The hydrocarbon solvent is not particularly limited, but, for example, may be at least one selected from the group consisting of n-pentane, n-hexane, n-heptane, isooctane, cyclohexane, toluene, benzene and xylene.

The organometallic compound may be an organic alkali metal compound or at least one selected from the group consisting of an organolithium compound, an organosodium compound, an organopotassium compound, an organorubidium compound and an organocesium compound.

Specifically, the organometallic compound may include at least one selected from the group consisting of methyllithium, ethyllithium, propyllithium, n-butyllithium, s-butyllithium, t-butyllithium, hexyllithium, n-decyllithium, t-octyllithium, phenyllithium, 1-naphthyllithium, n-eicosyllithium, 4-butylphenyllithium, 4-tolyllithium, cyclohexyllithium, 3,5-di-n-heptylcyclohexyllithium, 4-cyclopentyllithium, naphtylsodium, naphtylpotassium, lithium alkoxide, sodium alkoxide, potassium alkoxide, lithium sulfonate, sodium sulfonate, potassium sulfonate, lithium amide, sodium amide, potassium amide, and lithium isopropylamide.

The organometallic compound may be used in an amount of 0.01 mmol to 10 mmol based on total 100 g of the monomer. Specifically, the organometallic compound may be used in an amount of 0.05 mmol to 5 mmol, particularly 0.1 mmol to 3 mmol, and more particularly 0.1 mmol to 2 mmol, based on total 100 g of the monomer.

The substituted styrene-based compound represented by Formula 1 may be the same as that described above.

The substituted styrene-based compound represented by Formula 1 may be used in an amount of 0.1 wt % to 15 wt % based on the monomer. Specifically, the substituted styrene-based compound represented by Formula 1 may be used in an amount of 0.5 wt % to 5 wt % based on the monomer. For example, the substituted styrene-based compound may be used in the above amount ratio based on the aromatic vinyl-based monomer among the monomers. In a case in which the substituted styrene-based compound is used in an amount within the above range, the modification reaction may be optimally performed, and thus, a polymer having a high modification ratio may be obtained.

The polymerization reaction may be performed by further adding a polar additive if necessary, and the polar additive may be added in an amount of 0.001 g to 5 g, particularly 0.001 g to 1 g, and more particularly 0.005 g to 0.1 g, based on total 100 g of the monomer.

Also, the polar additive may be added in an amount of 0.1 mmol to 10 mmol, particularly 0.2 mmol to 5 mmol, and more particularly 0.5 mmol to 3 mmol, based on total 1 mmol of the organometallic compound.

The polar additive may be a salt, an ether, an amine, or a mixture thereof, and, particularly, may be at least one selected from the group consisting of tetrahydrofuran, ditetrahydrofurylpropane, diethylether, cycloamylether, dipropyl ether, ethylene dimethyl ether, diethylene glycol, dimethyl ether, tertiary butoxyethoxyethane, bis(3-dimethylaminoethyl) ether, (dimethylaminoethyl)ethylether, trimethylamine, triethylamine, tripropylamine, and tetramethylethylenediamine. For example, the polar additive may be ditetrahydropropylpropane, triethylamine, or tetramethylethylenediamine.

In a case in which the conjugated diene-based monomer and the aromatic vinyl-based monomer are copolymerized, since the above polar additive is used to compensate a difference in reaction rates of these monomers, the preparation method according to the embodiment of the present invention may induce so that the random copolymer may be easily formed.

The polymerization reaction may be an anionic polymerization reaction, and, specifically, may be living anionic polymerization in which an active site is obtained by a growth reaction by anions.

Furthermore, the polymerization may be temperature rise polymerization (adiabatic temperature rise polymerization), isothermal polymerization, or constant temperature polymerization (adiabatic polymerization).

Herein, the constant temperature polymerization denotes a polymerization method including a step of performing polymerization not by randomly applying heat but with its own reaction heat after the organometallic compound is added, the temperature rise polymerization denotes a polymerization method in which the temperature is increased by randomly applying heat after the organometallic compound is added, and the isothermal polymerization denotes a polymerization method in which the temperature of the polymer is constantly maintained by taking away heat or applying heat after the organometallic compound is added.

The polymerization may be performed in a temperature range of −20° C. to 200° C., particularly in a temperature range of 0° C. to 150° C., and more particularly in a temperature range of 10° C. to 120° C.

Step 2 is a step of reacting the active polymer with the modifier represented by Formula 2 to prepare a modified polymer.

The modifier represented by Formula 2 may be the same as that described above, and one or more types thereof may be mixed and used in the reaction.

The modifier represented by Formula 2 may be used in an amount of 0.1 mol to 10 mol based on 1 mol of the organometallic compound. Specifically, the modifier represented by Formula 2 may be used in an amount of 0.3 mol to 2 mol based on 1 mol of the organometallic compound.

The reaction of step 2 is a modification reaction for the introduction of a functional group into at least one end of the polymer, wherein the reaction may be performed in a temperature range of 0° C. to 90° C. for 1 minute to 5 hours.

Also, the method of preparing the modified polymer according to the embodiment of the present invention may be performed by a batch polymerization method or a continuous polymerization method including one or more reactors.

The preparation method according to the embodiment of the present invention may further include at least one step of recovering solvent and unreacted monomer and drying, if necessary, after the step of performing a polymerization reaction.

In the preparation method according to the embodiment of the present invention, a functional group may be introduced into the polymer main chain by polymerization of the substituted styrene-based compound represented by Formula 1 with the monomer, and a functional group may be further introduced into at least one end of the polymer by additionally performing a modification reaction with the modifier represented by Formula 2. Thus, the modified polymer, into which the above-described functional groups are introduced, may be prepared.

In addition, the present invention provides a rubber composition including the above modified polymer.

The rubber composition according to an embodiment of the present invention may include the modified polymer in an amount of 10 wt % or more, particularly 10 wt % to 100 wt %, and more particularly 20 wt % to 90 wt %. In a case in which the amount of the modified polymer is less than 10 wt %, an effect of improving abrasion resistance and crack resistance of a processed product, for example, a tire, prepared by using the rubber composition may be insignificant.

Furthermore, the rubber composition may further include other rubber components, if necessary, in addition to the modified polymer, and, in this case, the rubber component may be included in an amount of 90 wt % or less based on a total weight of the rubber composition. Specifically, the rubber component may be included in an amount of 1 part by weight to 900 parts by weight based on 100 parts by weight of the modified polymer.

The rubber component may be a natural rubber or a synthetic rubber, and, for example, the rubber component may be a natural rubber (NR) including cis-1,4-polyisoprene; a modified natural rubber, such as an epoxidized natural rubber (ENR), a deproteinized natural rubber (DPNR), and a hydrogenated natural rubber, in which the general natural rubber is modified or purified; and a synthetic rubber such as a styrene-butadiene rubber (SBR), polybutadiene (BR), polyisoprene (IR), a butyl rubber (IIR), an ethylene-propylene copolymer, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), a polysulfide rubber, an acrylic rubber, an urethane rubber, a silicon rubber, an epichlorohydrin rubber, a butyl rubber, and a halogenated butyl rubber. Any one thereof or a mixture of two or more thereof may be used.

Also, the rubber composition may include 0.1 part by weight to 200 parts by weight of a filler based on 100 parts by weight of the modified polymer, and, particularly, may include 10 parts by weight to 120 parts by weight of the filler.

The filler may be a silica-based filler, and the silica-based filler is not particularly limited, but, for example, may be wet silica (hydrous silicic acid), dry silica (anhydrous silicic acid), calcium silicate, aluminum silicate, or colloidal silica. For example, the filler may be wet silica in which an effect of improving both fracture characteristics and wet grip is the most significant.

Furthermore, the rubber composition according to the embodiment of the present invention may further include a carbon black-based filler, if necessary.

In a case in which silica is used as the filler, a silane coupling agent may be used together for the improvement of reinforcement and low heat generation property.

Specific examples of the silane coupling agent may be bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl) tetrasulfide, bis(2-trimethoxysilylethyl)tetrasulfide, 3-mercaptopropyl trimethoxysilane, 3-mercaptopropyl triethoxysilane, 2-mercaptoethyl trimethoxysilane, 2-mercaptoethyl triethoxysilane, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 3-trimethoxysilylpropyl benzothiazolyl tetrasulfide, 3-triethoxysilylpropyl benzolyl tetrasulfide, 3-triethoxysilylpropyl methacrylate monosulfide, 3-trimethoxysilylpropyl methacrylate monosulfide, bis(3-diethoxymethylsilylpropyl)tetrasulfide, 3-mercaptopropyl dimethoxymethylsilane, dimethoxymethylsilylpropyl-N,N-dimethylthiocarbamoyl tetrasulfide, or dimethoxymethylsilylpropyl benzothiazolyl tetrasulfide, and any one thereof or a mixture of two or more thereof may be used. For example, in consideration of the effect of improving the reinforcement, the silane coupling agent may be bis(3-triethoxysilylpropyl)polysulfide or 3-trimethoxysilylpropyl benzothiazyl tetrasulfide.

Also, in the rubber composition according to the embodiment of the present invention, since the modified polymer, in which a function group having a high affinity with the silica is introduced into the active site, is used as the rubber component, a mixing amount of the silane coupling agent may be reduced in comparison to a conventional case. Specifically, the silane coupling agent may be used in an amount of 1 part by weight to 20 parts by weight based on 100 parts by weight of the silica. In a case in which the silane coupling agent is used within the above range, the silane coupling agent may prevent gelation of the rubber component while sufficiently having an effect as a coupling agent. For example, the silane coupling agent may be used in an amount of 5 parts by weight to 15 parts by weight based on 100 parts by weight of the silica.

Also, the rubber composition according to the embodiment of the present invention may be sulfur cross-linkable, and, accordingly, may further include a vulcanizing agent.

The vulcanizing agent may specifically be sulfur powder, and may be included in an amount of 0.1 part by weight to 10 parts by weight based on 100 parts by weight of the rubber component. When the vulcanizing agent is included within the above range, elastic modulus and strength required for the vulcanized rubber composition may be secured and, simultaneously, a low fuel consumption property may be obtained.

Furthermore, the rubber composition according to the embodiment of the present invention may further include various additives, such as a vulcanization accelerator, process oil, a plasticizer, an antioxidant, a scorch inhibitor, zinc white, stearic acid, a thermosetting resin, or a thermoplastic resin, used in the general rubber industry, in addition to the above-described components.

The vulcanization accelerator is not particularly limited, but, specifically, a thiazole-based compound, such as 2-mercaptobenzothiazole (M), dibenzothiazyl disulfide (DM), and N-cyclohexylbenzothiazole-2-sulfenamide (CZ), or a guanidine-based compound, such as diphenylguanidine (DPG), may be used. The vulcanization accelerator may be included in an amount of 0.1 part by weight to 5 parts by weight based on 100 parts by weight of the rubber component.

Also, the process oil acts as a softener in the rubber composition, wherein the process oil may be a paraffin-based, naphthenic-based, or aromatic-based compound, and, for example, the aromatic-based compound may be used in consideration of tensile strength and abrasion resistance, and the naphthenic-based or paraffin-based process oil may be used in consideration of hysteresis loss and low temperature characteristics. The process oil may be included in an amount of 100 parts by weight or less based on 100 parts by weight of the rubber component, and, when the process oil is included in the above amount, decreases in tensile strength and low heat generation property (low fuel consumption property) of the vulcanized rubber may be prevented.

Furthermore, specific examples of the antioxidant may be N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, or a high-temperature condensate of diphenylamine and acetone. The antioxidant may be used in an amount of 0.1 part by weight to 6 parts by weight based on 100 parts by weight of the rubber component.

The rubber composition according to the embodiment of the present invention may be obtained by kneading the above mixing formulation using a kneader such as a Banbury mixer, a roll, and an internal mixer, and a rubber composition having excellent abrasion resistance as well as low heat generation property may also be obtained by a vulcanization process after molding.

Accordingly, the rubber composition may be suitable for the preparation of each member of a tire, such as a tire's tread, an under tread, a sidewall, a carcass coating rubber, a belt coating rubber, a bead filler, a chafer, or a bead coating rubber, or various industrial rubber products such as an anti-vibration rubber, a belt conveyor, and a hose.

Furthermore, the present invention provides a molded article prepared by using the rubber composition.

The molded article may include a tire or a tire's tread.

Hereinafter, the present invention will be described in more detail, according to specific examples and experimental examples. However, the following examples and experimental examples are merely presented to exemplify the present invention, and the scope of the present invention is not limited thereto.

Preparation Example 1: Preparation of 1-(2-methoxyethoxy)-4-vinylbenzene (1) Preparation of Hydroxystyrene 0.275 mol of sodium hydroxide was put in a 500 ml round-bottom flask and dissolved by adding 60 ml of anhydrous ethanol thereto, and 0.065 mol of acetoxystyrene was then added thereto and stirred for 4 hours in a nitrogen atmosphere at room temperature. Thereafter, 50 ml of distilled water was added and 30 ml of acetyl acetate was added to extract an organic layer, and the organic layer extraction was repeated three times. Anhydrous magnesium sulfate was added to dry and filter the extracted organic layer so that remaining moisture was removed. Thereafter, the solvent was removed under reduced pressure to obtain 7.54 g (96% yield) of yellow solid hydroxystyrene. $^1$H nuclear magnetic resonance spectroscopic data of the purified hydroxystyrene are as follows.

¹H-NMR (500 MHz, CDCl₃) δ 7.31-7.29 (d, J=9.5, 1H), δ 6.80-6.78 (d, J=8.5, Ar—H, 2H), δ 6.68-6.62 (q, J=9.5, 1H), δ 5.62-5.58 (d, J=17.5, 1H), δ 5.13-5.11 (d, J=11, 1H), δ 4.75 (s, 1H).

(2) Preparation of 1-(2-methoxyethoxy)-4-vinylbenzene 0.058 mmol of the hydroxystyrene was put in a 500 ml round-bottom flask and dissolved by adding 50 ml of acetonitrile, and 0.071 mol of potassium t-butoxide was added dropwise thereto and then refluxed for 1 hour. Thereafter, 0.076 ml of 2-chloroethylmethylether was slowly added dropwise thereto and then refluxed for 6 hours in a nitrogen atmosphere to perform a reaction. After the completion of the reaction, neutralization was performed using a hydrochloric acid aqueous solution, an organic layer was then extracted with an ethyl acetate/saturated base solution, and the organic layer was dried and filtered with anhydrous magnesium sulfate to remove remaining moisture. Thereafter, the solvent was removed under reduced pressure to obtain 9.9 g (95%) of a light brown liquid title compound of the following Formula (i). ¹H nuclear magnetic resonance spectroscopic data of the purified 1-(2-methoxyethoxy)-4-vinylbenzene are as follows.

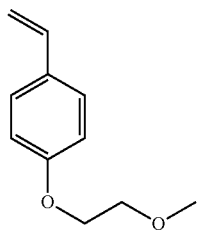

(i)

¹H-NMR (500 MHz, CDCl₃) δ 7.33-7.31 (d, J=9, Ar—H, 2H), δ 6.88-6.86 (d, J=8.5, Ar—H, 2H), δ 6.67-6.61 (q, J=9.5, 1H), δ 5.61-5.57 (d, J=17.5, 1H), δ 5.12-5.10 (d, J=11, 1H), δ 4.10-4.08 (t, J=4.5, 2H), δ 3.73-3.71 (t, J=4.75, 2H), δ 3.43 (s, 3H).

Preparation Example 2: Preparation of 1-(2-(2-methoxyethoxy)ethoxy)-4-vinylbenzene (1) Preparation of Hydroxystyrene 0.275 mol of sodium hydroxide was put in a 500 ml round-bottom flask and dissolved by adding 60 ml of anhydrous ethanol thereto, and 0.065 mol of acetoxystyrene was then added thereto and stirred for 4 hours in a nitrogen atmosphere at room temperature. Thereafter, 50 ml of distilled water was added and 30 ml of acetyl acetate was added to extract an organic layer, and the organic layer extraction was repeated three times. Anhydrous magnesium sulfate was added to dry and filter the extracted organic layer so that remaining moisture was removed. Thereafter, the solvent was removed under reduced pressure to obtain 7.54 g (96% yield) of yellow solid hydroxystyrene. ¹H nuclear magnetic resonance spectroscopic data of the purified hydroxystyrene are as follows.

¹H-NMR (500 MHz, CDCl₃) δ 7.31-7.29 (d, J=9.5, 1H), δ 6.80-6.78 (d, J=8.5, Ar—H, 2H), δ 6.68-6.62 (q, J=9.5, 1H), δ 5.62-5.58 (d, J=17.5, 1H), δ 5.13-5.11 (d, J=11, 1H), δ 4.75 (s, 1H).

(2) Preparation of 1-(2-(2-methoxyethoxy)ethoxy)-4-vinylbenzene 0.058 mmol of the hydroxystyrene was put in a 500 ml round-bottom flask and dissolved by adding 50 ml of acetonitrile, and 0.071 mol of potassium t-butoxide was added dropwise thereto and then refluxed for 1 hour. Thereafter, 0.076 ml of 1-bromo-2-(2-methoxyethoxy)ethane was slowly added dropwise thereto and then refluxed for 6 hours in a nitrogen atmosphere to perform a reaction. After the completion of the reaction, neutralization was performed using a hydrochloric acid aqueous solution, an organic layer was then extracted with an ethyl acetate/saturated base solution, and the organic layer was dried and filtered with anhydrous magnesium sulfate to remove remaining moisture. Thereafter, the solvent was removed under reduced pressure to obtain 10 g (96%) of a light brown liquid title compound of the following Formula (ii). ¹H nuclear magnetic resonance spectroscopic data of the purified 1-(2-(2-methoxyethoxy)ethoxy)-4-vinylbenzene of Formula (ii) are as follows.

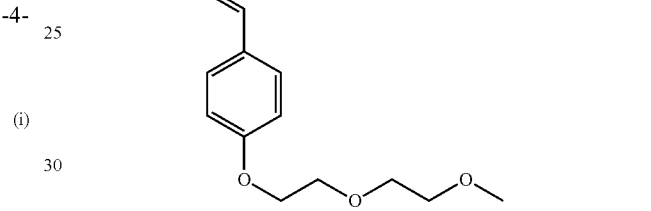

(ii)

¹H-NMR (500 MHz, CDCl₃) δ 7.33-7.32 (d, J=8.5, Ar—H, 2H), δ 6.88-6.86 (d, J=8.5, Ar—H, 2H), δ 6.68-6.62 (q, J=9.5, 1H), δ 5.62-5.58 (d, J=17.5, 1H), δ 5.13-5.10 (d, J=11, 1H), δ 4.15-4.13 (t, J=5, 2H), δ 3.87-3.85 (t, J=5, 2H), δ 3.73-3.71 (t, J=4.7, 2H), δ 3.59-3.57 (t, J=4.5, 2H), δ 3.39 (s, 3H).

Preparation Example 3: Preparation of diethyl 3,3'-((3-(triethoxysilyl)propyl)azanediyl)dipropionate 23.26 mmol of (3-aminopropyl)triethoxysilane was put in a 50 ml round-bottom flask and dissolved by adding 10 ml of ethanol thereto, and 46.53 mmol of ethyl acrylate was then added thereto and stirred for 24 hours in a nitrogen atmosphere at 80° C. to perform a reaction. After the completion of the reaction, the solvent was removed under reduced pressure, and distillation under reduced pressure was then performed at 80° C. to obtain 22.36 mmol (96.1% yield) of diethyl 3,3'-((3-(triethoxysilyl)propyl)azanediyl) dipropionate of Formula (iii). ¹H nuclear magnetic resonance spectroscopic data of the purified 3,3'-((3-(triethoxysilyl)propyl)azanediyl)dipropionate are as follows.

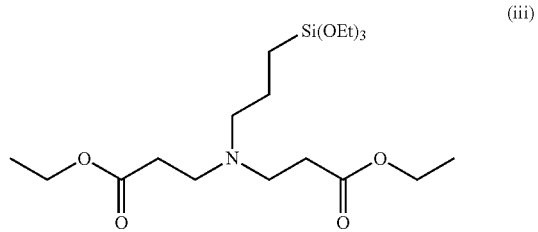

(iii)

$^1$H-NMR (500 MHz, CDCl$_3$) δ 4.07-4.03 (m, 4H), δ 3.77-3.72 (m, 6H), δ2.72-2.69 (t, 4H), δ 1.49-1.43 (m, 2H), δ 1.20-1.14 (m, 15H), δ 0.52-0.49 (t, 2H)

Example 1: Preparation of Modified Styrene-Butadiene Copolymer 270 g of styrene, 710 g of 1,3-butadiene, and 4 g of the substituted styrene-based compound prepared in Preparation Example 1 were added to a 20 L autoclave reactor, 5 kg of anhydrous n-hexane and 0.75 g of 2,2-bis(2-oxoranyl)propane (DTP), as a polar additive, were added, and an internal temperature of the reactor was then increased to 40° C. When the internal temperature of the reactor reached 40° C., 34 g (2.62 wt % in hexane, 33% activation) of n-butyllithium was added to the reactor to perform an adiabatic heating reaction. After 30 minutes, 20 g of 1,3-butadiene was added to cap polymer ends with butadiene. After 5 minutes, the modifier prepared in Preparation Example 3 was added and reacted for 15 minutes ([DTP]/[act. Li]=1.36 molar ratio, [modifier]/[act. Li]=1.7 molar ratio). Thereafter, the reaction was stopped by using ethanol and 33 g of a solution, in which 30 wt % of Wingstay K, as an antioxidant, was dissolved in hexane, was added. A polymer thus obtained was put in water heated by steam and stirred to remove the solvent, and was then roll-dried to remove the remaining solvent and water to prepare a modified styrene-butadiene copolymer.

Example 2: Preparation of Modified Styrene-Butadiene Copolymer

A modified styrene-butadiene copolymer was prepared in the same manner as in Example 1 except that the substituted styrene-based compound prepared in Preparation Example 2 was used instead of the substituted styrene-based compound prepared in Preparation Example 1 and the modifier was used at a molar ratio of [modifier]/[act. Li] of 1.9.

Comparative Example: Preparation of Styrene-Butadiene Copolymer 270 g of styrene and 710 g of 1,3-butadiene were added to a 20 L autoclave reactor, 5 kg of anhydrous n-hexane and 0.75 g of 2,2-bis(2-oxoranyl)propane (DTP), as a polar additive, were added, and an internal temperature of the reactor was then increased to 40° C. When the internal temperature of the reactor reached 40° C., 34 g (2.62 wt % in hexane, 33% activation) of n-butyllithium was added to the reactor to perform an adiabatic heating reaction. After 30 minutes, 20 g of 1,3-butadiene was added to cap polymer ends with butadiene. Thereafter, the reaction was stopped by using ethanol and 33 g of a solution, in which 30 wt % of Wingstay K, as an antioxidant, was dissolved in hexane, was added. A polymer thus obtained was put in water heated by steam and stirred to remove the solvent, and was then roll-dried to remove the remaining solvent and water to prepare a styrene-butadiene copolymer.

Reference Example 1: Preparation of Modified Styrene-Butadiene Copolymer

A modified styrene-butadiene copolymer was prepared in the same manner as in Example 1 except that the modifier prepared in Preparation Example 3 was not used.

Reference Example 2: Preparation of Modified Styrene-Butadiene Copolymer

A modified styrene-butadiene copolymer was prepared in the same manner as in Example 2 except that the modifier prepared in Preparation Example 3 was not used.

Experimental Example

In order to comparatively analyze physical properties of each copolymer prepared in Examples 1 and 2, Comparative Example, and Reference Examples 1 and 2, components, a weight-average molecular weight (Mw), a number-average molecular weight (Mn), a molecular weight distribution (Mw/Mn), and a maximum peak molecular weight (Mp) were respectively measured. The results thereof are presented in Table 1 below.

(1) Component Analysis

With respect to the component analysis, amounts of a styrene monomer (St) and vinyl were measured using nuclear magnetic resonance (NMR).

(2) Gel Permeation Chromatograph (GPC) Analysis

The weight-average molecular weight (Mw), the number-average molecular weight (Mn), and the maximum peak molecular weight (Mp) were measured by GPC analysis at a temperature of 40° C., and the molecular weight distribution (polydispersity index (PDI), Mw/Mn) was obtained by calculation using the measured weight-average molecular weight and number-average molecular weight. Specifically, with respect to the GPC, two PLgel Olexis columns (Polymer Laboratories) and one PLgel mixed-C column (Polymer Laboratories) were combined and used, all newly replaced columns were mixed-bed type columns, and polystyrene (PS) was used as a GPC standard material for the calculation of the molecular weight.

TABLE 1

| Category | BD:St:vinyl (molar ratio) | Mn (g/mol) | Mw (g/mol) | PDI (Mw/Mn) | Mp(g/mol, combination ratio wt %) | |
|---|---|---|---|---|---|---|
| | | | | | Mp$_1$ | Mp$_2$ |
| Example 1 | 24.5:29.4:47.3 | 629,724 | 1,011,008 | 1.6 | 625,667(59.8) | 1,430,788(40.2) |
| Example 2 | 21.7:30.9:47.4 | 484,788 | 813,177 | 1.67 | 681,850(78.7) | 1,564,345(21.3) |
| Comparative Example | 28.3:27.3:44.4 | 321,920 | 340,025 | 1.05 | 342,553 | — |
| Reference Example 1 | 23.6:29.1:47.3 | 513,230 | 642,022 | 1.25 | 611,461 | — |
| Reference Example 2 | 21.6:30.8:47.6 | 433,836 | 613,646 | 1.41 | 685,777 | — |

As illustrated in Table 1, it was confirmed that the modified styrene-butadiene copolymers of Examples 1 and 2 prepared by using the substituted styrene-based compound and modifier according to the present invention had a significantly increased coupling efficiency of the polymer components in comparison to the typical styrene-butadiene copolymer of Comparative Example and the modified styrene-butadiene copolymers of Reference Examples 1 and 2 prepared by only using the substituted styrene-based compound.

Specifically, relatively low molecular weight components were only present in each copolymer of Comparative Example and Reference Examples 1 and 2, and the modified styrene-butadiene copolymers of Examples 1 and 2 had a coupling efficiency of the polymer components of 40.2% and 21.3%, respectively.

The results indicated that a highly modified polymer was formed by using the substituted styrene-based compound and the modifier together.

The invention claimed is:

1. A modified polymer comprising a unit derived from a substituted styrene-based compound represented by Formula 1 and a unit derived from a modifier represented by Formula 2:

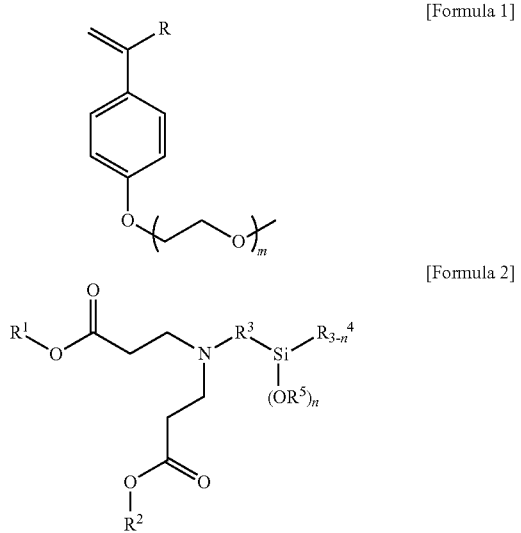

[Formula 1]

[Formula 2]

wherein, in Formula 1,
R is a hydrogen atom or a monovalent hydrocarbon group having 1 to 20 carbon atoms, and
m is an integer of 1 to 11, and
in Formula 2,
$R^1$ and $R^2$ are each independently a monovalent hydrocarbon group having 1 to 20 carbon atoms, or a monovalent hydrocarbon group having 1 to 20 carbon atoms which includes at least one heteroatom selected from the group consisting of nitrogen (N), sulfur (S), and oxygen (O),
$R^3$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms,
$R^4$ and $R^5$ are each independently a monovalent hydrocarbon group having 1 to 20 carbon atoms, and
n is an integer of 1 to 3.

2. The modified polymer of claim 1, wherein, in Formula 1,
R is a hydrogen atom, an alkyl group having 1 to 20 carbon atoms, a cycloalkyl group having 3 to 20 carbon atoms, an aryl group having 6 to 20 carbon atoms, an arylalkyl group having 7 to 20 carbon atoms, an alkoxy group having 1 to 20 carbon atoms, an alkoxyalkyl group having 2 to 20 carbon atoms, or a phenoxyalkyl group having 7 to 20 carbon atoms.

3. The modified polymer of claim 1, wherein, in Formula 1,
R is a hydrogen atom.

4. The modified polymer of claim 1, wherein, in Formula 2,
$R^1$ and $R^2$ are each independently one selected from the group consisting of an alkyl group having 1 to 10 carbon atoms, a cycloalkyl group having 3 to 12 carbon atoms, an aryl group having 6 to 12 carbon atoms, an arylalkyl group having 7 to 12 carbon atoms, and an alkoxyalkyl group having 2 to 10 carbon atoms,
$R^3$ is an alkylene group having 1 to 6 carbon atoms, and
$R^4$ and $R^5$ are each independently an alkyl group having 1 to 10 carbon atoms.

5. The modified polymer of claim 1, wherein, in Formula 2,
$R^1$ and $R^2$ are each independently an alkyl group having 1 to 10 carbon atoms or an alkoxyalkyl group having 2 to 10 carbon atoms,
$R^3$ is an alkylene group having 1 to 3 carbon atoms,
$R^4$ and $R^5$ are each independently an alkyl group having 1 to 5 carbon atoms, and
n is 2 or 3.

6. The modified polymer of claim 1, wherein the modified polymer is a homopolymer including an aromatic vinyl-based monomer-derived unit.

7. The modified polymer of claim 1, wherein the modified polymer is a copolymer including a conjugated diene-based monomer-derived unit and an aromatic vinyl-based monomer-derived unit.

8. The modified polymer of claim 1, wherein the modified polymer comprises an aromatic vinyl-based monomer-derived unit in an amount of 10 wt % or more.

9. The modified polymer of claim 1, wherein the modified polymer has a molecular weight distribution (Mw/Mn) of 1.01 to 10.

10. The modified polymer of claim 1, wherein the modified polymer has a vinyl content of 5 wt % or more.

11. The modified polymer of claim 1, wherein the modified polymer has a weight-average molecular weight of 10,000 g/mol to 2,000,000 g/mol.

12. A method of preparing the modified polymer of claim 1, the method comprising steps of:
(1) performing a polymerization reaction of a monomer with a substituted styrene-based compound represented by Formula 1 in a hydrocarbon solvent in the presence of an organometallic compound to prepare an active polymer coupled with an organometal; and (2) reacting the active polymer with a modifier represented by Formula 2:

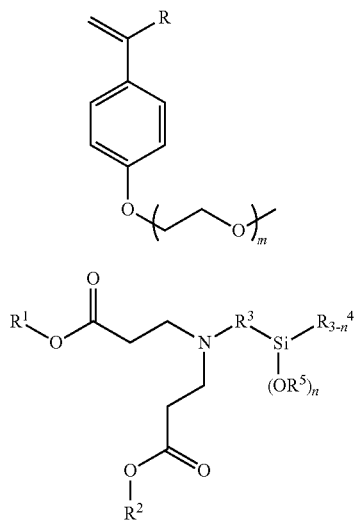

[Formula 1]

[Formula 2]

wherein,
in Formula 1,
R is a hydrogen atom or a monovalent hydrocarbon group having 1 to 20 carbon atoms, and
m is an integer of 1 to 11, and
in Formula 2,
$R^1$ and $R^2$ are each independently a monovalent hydrocarbon group having 1 to 20 carbon atoms, or a monovalent hydrocarbon group having 1 to 20 carbon atoms which includes at least one heteroatom selected from the group consisting of nitrogen (N), sulfur (S), and oxygen (O),
$R^3$ is a divalent hydrocarbon group having 1 to 20 carbon atoms which is substituted or unsubstituted with at least one substituent selected from the group consisting of an alkyl group having 1 to 20 carbon atoms, a cycloalkyl group having 3 to 20 carbon atoms, and an aryl group having 6 to 30 carbon atoms,
$R^4$ and $R^5$ are each independently a monovalent hydrocarbon group having 1 to 20 carbon atoms, and
n is an integer of 1 to 3.

13. The method of claim 12, wherein the organometallic compound is used in an amount of 0.01 mmol to 10 mmol based on total 100 g of the monomer.

14. The method of claim 12, wherein the organometallic compound comprises at least one selected from the group consisting of methyllithium, ethyllithium, propyllithium, n-butyllithium, s-butyllithium, t-butyllithium, hexyllithium, n-decyllithium, t-octyllithium, phenyllithium, 1-naphthyllithium, n-eicosyllithium, 4-butylphenyllithium, 4-tolyllithium, cyclohexyllithium, 3,5-di-n-heptylcyclohexyllithium, 4-cyclopentyllithium, naphtylsodium, naphtylpotassium, lithium alkoxide, sodium alkoxide, potassium alkoxide, lithium sulfonate, sodium sulfonate, potassium sulfonate, lithium amide, sodium amide, potassium amide, and lithium isopropylamide.

15. The method of claim 12, wherein the monomer is an aromatic vinyl-based monomer, or a mixture of an aromatic vinyl-based monomer and a conjugate diene-based monomer.

16. The method of claim 12, wherein the polymerization of step (1) is performed by further adding a polar additive.

17. The method of claim 16, wherein the polar additive is used in an amount of 0.1 mmol to 10 mmol based on total 1 mmol of the organometallic compound.

18. The method of claim 12, wherein,
in Formula 1,
R is a hydrogen atom, and
in Formula 2,
$R^1$ and $R^2$ are each independently an alkyl group having 1 to 10 carbon atoms or an alkoxyalkyl group having 2 to 10 carbon atoms,
$R^3$ is an alkylene group having 1 to 3 carbon atoms,
$R^4$ and $R^5$ are each independently an alkyl group having 1 to 5 carbon atoms, and
n is 2 or 3.

19. The method of claim 12, wherein the substituted styrene-based compound represented by Formula 1 is used in an amount of 0.1 wt % to 15 wt % based on the monomer.

20. The method of claim 12, wherein the modifier represented by Formula 2 is used in an amount of 0.1 mol to 10 mol based on 1 mol of the organometallic compound.

* * * * *